United States Patent
Burgos et al.

(10) Patent No.: US 7,365,212 B2
(45) Date of Patent: Apr. 29, 2008

(54) METHOD FOR THE IN SITU PREPARATION OF CHIRAL COMPOUNDS DERIVED FROM OXAZABOROLIDINE-BORANE COMPLEXES WHICH ARE USED IN ASYMMETRIC REDUCTION REACTIONS

(75) Inventors: Alain Burgos, Les Ponts-de-Cé (FR); Blandine Bertrand, Angrie (FR); Stéphane Frein, Saint-Aubin-de-Luigné (FR); Jean-François Pluvie, Angers (FR); Sonia Roussiasse, Champigne (FR)

(73) Assignee: ZaCh System S.p.A., Milan (IT)

( * ) Notice: Subject to any disclaimer, the term of this patent is extended or adjusted under 35 U.S.C. 154(b) by 189 days.

(21) Appl. No.: 10/574,871

(22) PCT Filed: Oct. 11, 2004

(86) PCT No.: PCT/FR2004/002573

§ 371 (c)(1),
(2), (4) Date: Apr. 6, 2006

(87) PCT Pub. No.: WO2005/035540

PCT Pub. Date: Apr. 21, 2005

(65) Prior Publication Data

US 2007/0055068 A1    Mar. 8, 2007

(30) Foreign Application Priority Data

Oct. 9, 2003   (FR) ................................. 03 11838

(51) Int. Cl.
*C07F 5/02* (2006.01)

(52) U.S. Cl. ..................................... 548/401; 548/405
(58) Field of Classification Search ................ 548/401, 548/405
See application file for complete search history.

(56) References Cited

U.S. PATENT DOCUMENTS 5,189,177 A    2/1993   Blacklock et al.
5,264,574 A   11/1993   Carroll et al.

FOREIGN PATENT DOCUMENTS

WO           94/26751        11/1994

OTHER PUBLICATIONS

Abiko et al. "An Improved, Convenient Procedure for Reduction of Amino Acids to Aminoalcohols: Use of $NaBH_4$-$H_2SO_4$," Tetrahedron Letters vol. 33, No. 38 p. 5517-5518.
Bell et al. "The Reduction of Organic Halogen Compounds by Sodium Borohydride" The Journal of Organic Chemistry, vol. 34 No. 12 Dec. 1969 p. 3923-3926.
Periasmy "New Organic Synthetic Methods Using the $NaBH_4$/$I_2$ System" ACS Symposium Series, 2001, 783 p. 65-78.

*Primary Examiner*—Kamal A Saeed
(74) *Attorney, Agent, or Firm*—Merchant & Gould P.C.

(57) ABSTRACT

A process for the in situ preparation of chiral compounds derived from oxazaborolidine-borane complexes, wherein a metal borohydride, a Lewis base and an inorganic acid ester are brought together and an optically active amino alcohol and optionally a halide are then added. The compound obtained is a complex that is useful as a catalyst in asymmetric reduction reactions. The reaction is performed by adding the substance to be reduced, particularly prochiral ketones or ether oximes, in order to synthesize chiral alcohols or chiral amines.

25 Claims, No Drawings

METHOD FOR THE IN SITU PREPARATION OF CHIRAL COMPOUNDS DERIVED FROM OXAZABOROLIDINE-BORANE COMPLEXES WHICH ARE USED IN ASYMMETRIC REDUCTION REACTIONS

The present invention relates to the implementation of a novel process for the in situ preparation of chiral compounds derived from oxazaborolidine-borane complexes which are used as catalysts in prochiral ketone reduction reactions for the synthesis of chiral alcohols or in ether oxime reductions for the synthesis of chiral amines.

The prior art described by the author Spehar A. et al. in the article "J. Org. Chem., 1969, 34(12), pp 3923-3926", discloses a process for the in situ generation of borane, from reactants such as sodium borohydride ($NaBH_4$) and dimethyl sulfate ($Me_2SO_4$), in carrying out an alkene hydroboration reaction for the preparation of alcohols.

This same process for the in situ generation of borane, referred to by the authors Abiko A. and Masamune S. in the article "Tetrahedron Letters, 1992, 33(38), pp 5517-5518", was also used in a reaction for the reduction of amino acid derivatives to synthesize amino alcohols.

More recently, in the journal "ACS Symposium Series, 2001, 783 (Organoborane for syntheses), pp 65-78", the author Periasamy M. published the in situ preparation of borane-Lewis base complexes and chiral compounds derived from oxazaborolidines, from reactants such as sodium borohydride ($NaBH_4$) and iodine ($I_2$), said chiral compounds being preferred catalysts in asymmetric reductions of prochiral ketones.

The factor which limits the latter process is the use of iodine in an industrial context, because, from the point of view of the working environment, substantial financial investment has to be made in order to handle it.

The Applicant has developed an industrial process for the in situ preparation of borane-Lewis base complexes and chiral compounds derived from oxazaborolidine-borane complexes which circumvents the problem of handling iodine. These chiral compounds derived from oxazaborolidine-borane complexes are known for their stereoselective performance when used in reduction processes.

The invention therefore relates to a process for the in situ preparation of chiral compounds derived from oxazaborolidine-borane complexes which are used as catalysts in reduction reactions for the synthesis of optically active alcohols or amines, characterized in that:

the following are added to a suspension of a metal borohydride defined by formula (I):

$$MBH_4 \quad (I)$$

in which:
M is in particular a sodium, potassium, lithium or zinc ion and preferably a sodium ion:
a) a Lewis base of general formula (II) below:

in which:
$R_1$ and $R_2$, which are identical or different, are a hydrogen atom, an optionally substituted, linear or branched alkyl, an optionally substituted aryl, an alkylaryl or a $C_4$-$C_7$ cycloalkyl, or
$R_1$ and $R_2$ together form a $C_1$-$C_7$ alkyl chain or an optionally substituted $C_2$-$C_7$ carbocycle;
n is equal to 1 or 2; and
A is a nitrogen, oxygen, sulfur or phosphorus atom.

In particular embodiments of the invention, the compound of formula (II) is a linear or cyclic ether, preferably tetrahydrofuran or tetrahydropyran; a secondary or tertiary amine, preferably N,N-dimethylamine, N,N-diethylamine, aniline, N,N-diethylaniline or N-ethyl-N-isopropylaniline; a linear or cyclic thioether, preferably dimethyl sulfide; an amino ether, preferably morpholine; or a phosphine, preferably triphenylphosphine.

In one preferred embodiment of the invention, the compound of formula (II) is N,N-diethylaniline (DEA).

b) an inorganic acid ester of general formula (III) below:

in which:
X is a sulfonyloxy ester group ($-OS(O)_2OR_4$), a sulfonate ($-OS(O)R_5$) or a sulfite ($-OS(O)OR_5$); and
$R_3$, $R_4$ and $R_5$, which are identical or different, are a linear or branched $C_{1-7}$ alkyl optionally substituted by a halogen atom, an aryl, a heterocycle, a heteroaryl, a $C_{1-7}$ alkoxy group, an alkyl($C_{1-7}$)-thio group, an alkyl($C_{1-7}$)-aryl group or a $C_4$-$C_7$ cycloalkyl, or
$R_4$ and $R_5$ together are a $C_1$-$C_7$ alkyl chain or an optionally substituted $C_2$-$C_7$ carbocycle.

In particular embodiments of the invention, the compound of general formula (III) is a dialkyl sulfate, a sulfuric acid bisaryloxyalkyl ester, a bisalkoxy-sulfonyloxyalkane or a dioxathiolane dioxide.

In one preferred embodiment of the invention, the compound of general formula (III) is dimethyl sulfate ($Me_2SO_4$).

In one advantageous embodiment of the process, the amounts of Lewis base and inorganic ester are between 1 and 2 equivalents, based on the metal borohydride.

In one preferred embodiment of the invention, the chosen amounts of DEA and $Me_2SO_4$ are 1.05 equivalents, based on $NaBH_4$.

The solvent used is a customary aprotic solvent.

Advantageously, the aprotic solvent is a non-amino solvent that is inert towards metal borohydride ($NaBH_4$) and borane ($BH_3$). Examples of non-amino solvents which may be mentioned are ethers such as tetrahydrofuran (THF) and dioxane, glymes such as ethylene glycol and dimethyl ether (DME), aromatic compounds such as toluene, or other solvents such as $CH_2Cl_2$.

The compounds (I), (II) and (III) are brought into contact at a temperature of between 0° C. and 75° C.

The resulting reaction medium is stirred at this temperature for a period of between 0.5 and 4 hours.

Finally, the order of addition of the compounds of formulae (I), (II) and (III) is given by way of indication and without implying a limitation.

This reaction forms a borane-Lewis base complex in solution, to which are added an optically active amino alcohol of general formula (IV) below and optionally a halide of formula (X) defined later:

in which:
$R_6$ is a hydrogen atom, a linear or branched $C_{1-8}$ lower alkyl group, preferably methyl, ethyl, n-propyl, isopropyl, n-butyl, isobutyl, sec-butyl, tert-butyl or pentyl, or a $C_{1-15}$ arylalkyl group, preferably benzyl, phenylethyl or methylbenzyl, which can optionally be substituted by a $C_{1-5}$ alkoxy or alkyl of the methyl, ethyl, n-propyl, isopropyl, n-butyl, sec-butyl, tert-butyl, pentyl, methoxy, ethoxy, propoxy, butoxy or pentoxy type;

$R_7$, $R_8$, $R_9$, $R_{10}$, $R_{11}$ and $R_{12}$, which are identical or different, independently are a hydrogen atom, organic radicals such as a $C_{1-8}$ lower alkyl group, especially of the methyl, ethyl, n-propyl, isopropyl, n-butyl, isobutyl, sec-butyl, tert-butyl or pentyl type, a $C_{6-12}$ aryl group, especially of the phenyl, 1-naphthyl or 2-naphthyl type, or a $C_{7-12}$ arylalkyl group, especially of the benzyl, phenylethyl or methyl-benzyl type, it being possible for said aryl or arylalkyl groups to be substituted by a $C_{1-5}$ alkyl or a group such as mentioned above, with the proviso that $R_6$ and $R_7$ are different;

$R_6$ and $R_7$, or $R_7$ and $R_{11}$, or $R_8$ and $R_9$, or $R_{10}$ and $R_{11}$ together can form an optionally substituted $C_{3-6}$ lower alkylene group, preferably a methylene, dimethylene, trimethylene or tetramethylene group;

$R_8$ and $R_9$ together can form an alkylene group that is optionally substituted or fused with a benzene ring, preferably trimethylene, tetramethylene, pentamethylene, o-phenylenemethylene or o-phenylenedimethylene;

n is equal to 0, 1, 2 or 3; and $C_1$ and/or $C_2$ and/or $C_3$ are an asymmetric carbon atom.

If n is equal to zero, preferred compounds of formula (IV) are the optically active beta-amino alcohols of general formula (IVa):

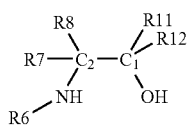

(IVa)

in which:

$R_6$ is a hydrogen atom, a linear or branched $C_{1-8}$ lower alkyl group, preferably methyl, ethyl, n-propyl, isopropyl, n-butyl, isobutyl, sec-butyl, tert-butyl or pentyl, or a $C_{1-15}$ arylalkyl group, e.g. benzyl, phenylethyl or methylbenzyl, which can optionally be substituted by a $C_{1-5}$ alkoxy or alkyl, especially of the methyl, ethyl, n-propyl, isopropyl, n-butyl, sec-butyl, tert-butyl, pentyl, methoxy, ethoxy, propoxy, butoxy or pentoxy type;

$R_7$, $R_8$ and $R_{11}$, which are identical or different, independently are a hydrogen atom, a $C_{1-8}$ lower alkyl group, especially of the methyl, ethyl, n-propyl, isopropyl, n-butyl, isobutyl, sec-butyl, tert-butyl or pentyl type, a $C_{6-12}$ aryl group, e.g. phenyl, 1-naphthyl or 2-naphthyl, or a $C_{7-12}$ arylalkyl group, preferably benzyl, phenylethyl or methylbenzyl, it being possible for said aryl or arylalkyl groups to be substituted, with the proviso that $R_7$ and $R_8$ are different;

$R_6$ and $R_7$ together can form an optionally substituted $C_{1-6}$ alkylene group, e.g. methylene, dimethylene, trimethylene or tetramethylene;

$R_8$ and $R_{11}$ together can form an alkylene group that is optionally substituted or fused with a benzene ring, e.g. trimethylene, tetramethylene, pentamethylene, o-phenylenemethylene or o-phenylenedimethylene; and $C_1$ and/or $C_2$ are an asymmetric carbon atom.

The optically active compounds of formula (IVa) listed below, using a customary nomenclature, are preferred embodiments of the invention:

norephedrine; ephedrine; 2-amino-1-(2,5-dimethylphenyl)-1-propanol; 2-amino-1-(2,5-dimethoxyphenyl)-1-propanol; 2-amino-1-(2,5-diethoxyphenyl)-1-propanol; 2-amino-1-(2,5-dipropoxyphenyl)-1-propanol; 2-amino-1-(2-methoxy-phenyl)-1-propanol; 2-amino-1-(2-ethoxyphenyl)-1-propanol; 2-amino-1-(2-propoxyphenyl)-1-propanol; 2-amino-1-(2-methylphenyl)-1-propanol; 2-amino-1-(2-methoxy-5-methylphenyl)-1-propanol; 2-amino-1-(4-methoxy-2-methylphenyl)-1-propanol; 2-amino-1-(2-ethoxy-5-methylphenyl)-1-propanol; 2-amino-1-(2,4-dimethylphenyl)-1-propanol; 2-amino-1-(2,4,6-trimethylphenyl)-1-propanol; 2-amino-1-(1-naphthyl)-1-propanol; 2-amino-1-(2-naphthyl)-1-propanol; 2-amino-1,2-diphenylethanol; 2-amino-1,1-diphenyl-1-propanol; 2-amino-1,1-diphenyl-3-methyl-1-butanol; 2-amino-1,1-diphenyl-4-methyl-1-propanol; 2-amino-3-methyl-1-butanol; 2-amino-4-methyl-1-pentanol; 2-amino-1-propanol; 2-amino-3-phenyl-1-propanol; 2-amino-2-phenyl-1-ethanol; 2-pyrrolidinylmethanol; α,α-diphenyl-2-pyrrolidinylmethanol; 2-piperidinemethanol; α,α-diphenyl-2-piperidinylmethanol; 2-aziridinylmethanol; α,α-diphenyl-2-aziridinylmethanol; 2-azetidinylmethanol; α,α-diphenyl-2-azetidinylmethanol; 2-aminocyclopentan-1-ol; 2-aminocyclohexan-1-ol; 1-aminoindan-2-ol; 3-amino-2-hydroxybomane.

The optically active compound α,α-diphenyl-2-pyrrolidinylmethanol is particularly preferred.

If n is equal to 1, preferred compounds of formula (IV) are optically active gamma-amino alcohols of formula (IVb):

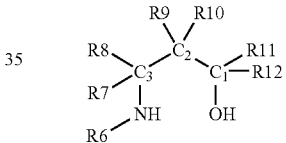

(IVb)

in which:

$R_6$ is a hydrogen atom, a linear or branched $C_{1-8}$ lower alkyl group, especially of the methyl, ethyl, n-propyl, isopropyl, n-butyl, isobutyl, sec-butyl, tert-butyl or pentyl type, or a $C_{1-15}$ arylalkyl group, e.g. benzyl, phenylethyl or methylbenzyl, which can optionally be substituted by a $C_{1-5}$ alkoxy or alkyl, especially of the methyl, ethyl, n-propyl, isopropyl, n-butyl, sec-butyl, tert-butyl, pentyl, methoxy, ethoxy, propoxy, butoxy or pentoxy type;

$R_6$, $R_7$, $R_8$, $R_9$, $R_{10}$, $R_{11}$, and $R_{12}$, which are identical or different, independently are a hydrogen atom, a $C_{1-8}$ lower alkyl group, especially of the methyl, ethyl, n-propyl, isopropyl, n-butyl, isobutyl, sec-butyl, tert-butyl or pentyl type, a $C_{6-12}$ aryl group, especially phenyl, 1-naphthyl or 2-naphthyl, or a $C_{7-12}$ arylalkyl group, especially benzyl, phenylethyl or methylbenzyl, it being possible for said aryl or arylalkyl groups to be substituted, with the proviso that $R_7$ and $R_8$ are different;

$R_6$ and $R_7$ together can form an optionally substituted $C_{3-6}$ lower alkylene group, especially methylene, dimethylene, trimethylene or tetramethylene;

$R_8$,$R_{11}$ or $R_8$,$R_9$ or $R_9$,$R_{11}$ together can form an alkylene group that is optionally substituted or fused with a benzene ring, especially trimethylene, tetra-methylene, pentamethylene, o-phenylenemethylene or o-phenylenedimethylene; and $C_1$ and/or $C_2$ and/or $C_3$ are an asymmetric carbon atom.

The optically active gamma-amino alcohols listed below using a customary nomenclature are particular embodiments of the invention:

β,β-diphenyl-2-pyrrolidinylethanol; β,β-di(t-butyl)-2-piperidinylethanol; 2-phenyl-4-hydroxypiperidine.

If n is equal to 2, preferred compounds of formula (IV) are derivatives of an optically active delta-amino alcohol of formula (IVc):

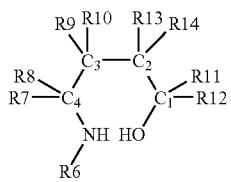

(IVc)

in which:

$R_6$ is a hydrogen atom, a linear or branched $C_{1-8}$ alkyl group, especially a methyl, ethyl, n-propyl, isopropyl, n-butyl, isobutyl, sec-butyl, tert-butyl or pentyl group, or a $C_{1-15}$ arylalkyl group, especially benzyl, phenylethyl or methylbenzyl, which can optionally be substituted by a $C_{1-5}$ alkoxy or alkyl, especially a methyl, ethyl, n-propyl, isopropyl, n-butyl, sec-butyl, tert-butyl, pentyl, methoxy, ethoxy, propoxy, butoxy or pentoxy group;

$R_7$, $R_8$, $R_9$, $R_{10}$, $R_{11}$, $R_{12}$, $R_{13}$ and $R_{14}$, which are identical or different, independently are a hydrogen atom, a $C_{1-8}$ lower alkyl group, especially a methyl, ethyl, n-propyl, isopropyl, n-butyl, isobutyl, sec-butyl, tert-butyl or pentyl group, a $C_{6-12}$ aryl group, especially a phenyl, 1-naphthyl or 2-naphthyl group, or a $C_{7-12}$ arylalkyl group, e.g. benzyl, phenylethyl or methylbenzyl, it being possible for said aryl or arylalkyl groups to be substituted by a $C_{1-5}$ alkyl or a group such as those mentioned above, with the proviso that $R_7$ and $R_8$ are different;

$R_6$ and $R_7$ together can form an optionally substituted $C_{3-6}$ lower alkylene group, especially a methylene, dimethylene, trimethylene or tetramethylene group;

$R_9$ and $R_8$ together can form an alkylene group that is optionally substituted or fused with a benzene ring, e.g. trimethylene, tetramethylene, pentamethylene, o-phenylenemethylene or o-phenylenedimethylene; and $C_1$ and/or $C_2$ and/or $C_3$ and/or $C_4$ are an asymmetric carbon atom.

The optically active compound of formula (IV) may or may not be in solution, insofar as the solvent is capable of solubilizing the product and does not affect the reaction.

Advantageously, a halide of formula (X) below is added first to the borane-Lewis base complex, followed by the optically active amino alcohol of formula (IV) as defined above:

$$M_1-Y \quad (X)$$

in which:

Y is a halogen atom such as chlorine, bromine, fluorine or iodine; and $M_1$ is selected from a sodium, potassium or lithium ion, an ammonium group and a phosphonium group.

The Applicant has demonstrated that the addition of the compound of formula (X) makes it possible to perform the reaction with all the optically active amino alcohol compound of formula (IV). Furthermore, the addition of the compound of formula (X) makes it possible to avoid recycling the optically active amino alcohol compound of formula (IV) when the latter is used in an amount of less than 2% and with a high added value.

Consequently, the addition of the compound of formula (X) affords substantial economic gains by limiting the necessary amount of optically active amino alcohol compound of formula (IV).

Examples of ammonium groups which may be mentioned are tetraalkylammonium, pyridinium, alkylpiperidinium, alkylpiperazinium, alkyl-pyrrolidinium and tetraalkylanilinium groups. The term alkyl denotes a linear or branched $C_{1-7}$ alkyl chain in this case.

Examples of phosphonium groups which may be mentioned are aryl-phosphonium or alkylarylphosphonium groups such as tetrakis(dimethylamino)-phosphonium, tetraphenylphosphonium, triphenylphosphonium and benzyltriphenylphosphonium.

The addition of the compound of formula (IV) and optionally of the compound of formula (X) takes place at a temperature of between 0° C. and 75° C. and the reaction medium is kept at this temperature for a period of between 0.5 and 4 hours, with stirring.

In one advantageous embodiment of the process, the amount of compound derived from an optically active beta-amino alcohol of formula (IV) is between 0.005 and 0.2 equivalent, preferably 0.008 equivalent, based on the metal borohydride.

In one preferred embodiment of the invention, the derivative of formula (IV) is optically active α,α-diphenyl-2-pyrrolidinylmethanol and it is added in an amount of between 0.008 and 0.016 equivalent, based on $NaBH_4$.

In one advantageous embodiment of the process, the amount of halide of formula (X) is between 0.05 and 1.25 equivalents, preferably 0.2 equivalent, based on the compound of formula (VI).

In one preferred embodiment of the invention, the halide of general formula (X) is lithium chloride (LiCl).

In the Applicant's process, the complexes thus prepared in situ are chiral compounds of formula (V):

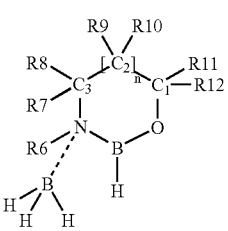

(V)

in which:

$R_6$, $R_7$, $R_8$, $R_9$, $R_{10}$, $R_{11}$, $R_{12}$ and n are as defined in formula (IV) and $C_1$ and/or $C_2$ and/or $C_3$ are an asymmetric carbon atom.

If n is equal to 0, the preferred compounds are optically active oxazaborolidine-borane complexes of formula (Va):

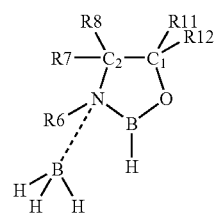

(Va)

in which:

$R_6$, $R_7$, $R_8$, $R_{11}$, $R_{12}$ and $C_1$ and/or $C_2$ are as defined in formula (IVa).

$C_1$ and/or $C_2$ are an asymmetric carbon.

If n is equal to 1, the preferred compounds are optically active oxazaborine-borane complexes of formula (Vb):

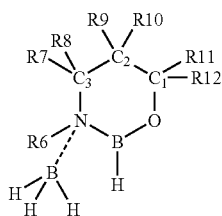

(Vb)

in which:

$R_6$, $R_7$, $R_8$, $R_9$, $R_{10}$, $R_{11}$ and $R_{12}$ are as defined in formula (IVb) and $C_1$ and/or $C_2$ and/or $C_3$ are an asymmetric carbon atom.

If n is equal to 2, the compounds of the invention are optically active oxazaborepine-borane complexes of general formula (Vc) below:

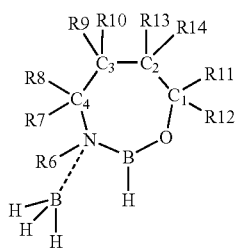

(Vc)

in which:

$R_6$, $R_7$, $R_8$, $R_9$, $R_{10}$, $R_{11}$, $R_{12}$, $R_{13}$ and $R_{14}$ are as defined in formula (IV) and $C_1$ and/or $C_2$ and/or $C_3$ and/or $C_4$ are an asymmetric carbon atom.

The resulting compounds of formula (V) are prepared in situ and used as such, as catalysts, in asymmetric reduction reactions for the synthesis of chiral alcohols or for the synthesis of chiral amines.

In particular, the complex of formula (V) prepared in situ is used for reducing the prochiral ketones of general formula (VI) to the corresponding optically active alcohols of general formula (VII):

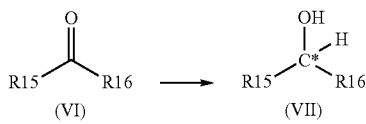

The compounds of formulae (VI) and (VII) are defined as follows:

$R_{15}$ and $R_{16}$ are different and the chirality of the secondary alcohol obtained is defined by the carbon atom carrying the alcohol group.

$R_{15}$ and $R_{16}$ are inert to reduction and are optionally substituted organic radicals which together can form a saturated or unsaturated ring.

Advantageously, $R_{15}$ and $R_{16}$, which are different, independently are an alkyl, alkenyl, alkynyl, unsaturated hydrocarbon, aryl or cycloalkyl group, an aryl-hydrocarbon or a heterocarbocycle, said groups optionally carrying one or more substituents represented by a halogen atom, an alkyl, aryl, alkoxy, aryloxy or heteroaryl group and an organic functional group.

Again advantageously, $R_{15}$ and $R_{16}$ together form a saturated or unsaturated ketonic carbocycle that may or may not comprise one or more heteroatoms. Said ketonic carbocycle optionally comprises one or more substituents represented by a halogen atom, an alkyl, aryl, alkoxy, aryloxy or heteroaryl group and an organic functional group. Said ketonic carbocycle is optionally fused with a cycloalkyl, aryl or heteroaryl group, said groups optionally carrying one or more substituents represented by a halogen atom, an alkyl, aryl, alkoxy, aryloxy or heteroaryl group and an organic functional group.

Examples of "alkyl" groups which may be mentioned are linear or branched, saturated, acyclic hydrocarbon groups having from 1 to 20 carbon atoms, such as the methyl, ethyl, n-propyl, isopropyl, tert-butyl, n-butyl or isobutyl group.

Examples of "alkenyl" groups which may be mentioned are linear or branched, unsaturated, acyclic hydrocarbon groups having 1 to 20 carbon atoms and containing one or more double bonds, such as the vinyl, ethylidienyl, allyl, isopropenyl, butenyl, butadienyl, allenyl or hexadienyl group.

Examples of "alkynyl" groups which may be mentioned are linear or branched, unsaturated, acyclic hydrocarbon groups having 2 to 20 carbon atoms and containing one or more triple bonds, such as ethylidynyl and propynyl groups.

Examples of "unsaturated hydrocarbon" groups which may be mentioned are linear or branched, unsaturated, cyclic or acyclic hydrocarbon groups having 2 to 20 carbon atoms and containing at the same time one or more double bonds and one or more triple bonds, such as hexadienynyl, pentenynyl and cyclodecenynyl groups.

Examples of "cyclic hydrocarbon" groups which may be mentioned are saturated or unsaturated, monocyclic or polycyclic hydrocarbon groups having 3 to 20 carbon atoms and containing one or more units of unsaturation in the form of double or triple bonds, such as cyclopropyl, cyclobutyl, cyclopentyl, cyclopentenyl, cyclopentadienyl, cyclohexyl, cyclohexenyl and cyclohexadienyl groups.

Examples of "aryl" groups which may be mentioned are monocyclic or fused polycyclic hydrocarbon groups having 6 to 35 carbon atoms, such as phenyl, naphthyl, phenanthryl, anthryl, pyrenyl, pentalenyl, biphenylenyl, azulenyl, azulenyl and acenaphthylenyl groups.

Examples of "aryl-hydrocarbon" groups which may be mentioned are alkyl, alkenyl and alkynyl groups substituted by an aryl group having 7 to 35 carbon atoms, such as benzyl, diphenylmethyl, cinnamyl, trityl and benzylidynyl.

Examples of "heterocarbocyclic" groups which may be mentioned are heteroaryl groups having 4 to 10 carbon atoms and containing one or more heteroatoms, such as thienyl, furyl, pyrrolyl, pyridyl, benzothienyl, carbazolyl, phenazinyl, isoxazolyl, imidazolinyl, pyrazinyl, pyrazolyl, pyrimidinyl, indolyl, isoindolyl, purinyl, quinolyl, isoquinolyl, benzofuryl and xanthenyl groups. Other examples of "heterocarbocyclic" groups which may be mentioned are unsaturated heterocycles having 4 to 10 carbon atoms and containing one or more heteroatoms, such as pyranyl, chromenyl, 2H-pyrrolyl, 3H-indolyl, pyrrolinyl, chromanyl, indolinyl and thiazolyl groups.

Examples of "heterocycloalkyl" groups which may be mentioned are saturated heterocyclic groups having 3 to 10 carbon atoms and containing one or more heteroatoms, such as imidazolidinyl, pyrrolidinyl, pyrazolidinyl, piperidyl, piperazinyl, indolinyl and morpholinyl groups.

Examples of "ketonic carbocyclic" groups which may be mentioned are cyclic groups having 5 to 20 carbon atoms, such as cyclopentanone, cyclo-pentenone, cyclohexanone, cyclohexenone, indanone, 3,4-dihydro-2H-naphthalen-1-one, 3,4-dihydro-1H-naphthalen-2-one, inden-1-one, acenaphthylen-1-one, acenaphthylen-2-one, fluoren-9-one, phenalen-1-one, phenalen-2-one, cyclohexane-1,3-dione, piperidin-3-one, piperidin-4-one, dihydropyran-3-one and tetrahydropyran-4-one.

Examples of "halogen" atoms which may be mentioned are chlorine, bromine, fluorine and iodine atoms.

The term "aryloxy" denotes an aryl group bonded to an oxygen atom.

The term "alkoxy" denotes an alkyl group bonded to an oxygen atom.

Examples of "heteroatoms" which may be mentioned are oxygen, nitrogen and sulfur atoms.

Examples of "organic functional groups" which may be mentioned are hydroxyl, amino, thiol, cyano (—CN), cyanato (—OCN), ether (—OR$_{19}$), substituted amino (—NHR$_{19}$, —NR$_{19}$R$_{20}$, —NHOH, —NHOR$_{19}$, —NHSO$_2$R$_{19}$), imino (=NR$_{19}$), ester (—COOR$_{19}$), amido (—CONH$_2$, —CONHR$_{19}$, —CONR$_{19}$R$_{20}$), nitro (—NO$_2$), nitroso (—NO), thioether (—SR$_{19}$), sulfoxide (—SOR$_{19}$), sulfone (—SO$_2$R$_{19}$), sulfonyloxy (—OSO$_2$R$_{19}$), carbonyldioxy (—OC(O)OR$_{19}$), carbonyloxy (—OCOR$_{19}$), dioxy (—OCH$_2$O—, —OR$_{19}$O—), silyl (—Si(R$_{19}$)$_3$), silyloxy (—OSiR$_{19}$R$_{20}$R$_{21}$, —OSiR$_{19}$R$_{20}$O—), . . . (—PO(OR$_{19}$)$_2$) and dithioether (—SR$_{19}$S—) groups.

R$_{19}$, R$_{20}$ and R$_{21}$ can be identical or different and are defined in the same way as R$_{16}$.

R$_{19}$ and R$_{20}$ together can form a heterocarbocycle or a heterocycloalkyl.

The ketone can be used in a neutral or ionic (ammonium) form.

By way of indication and without implying a limitation, the prochiral ketones which can be reduced by the complex formed in situ according to the invention are as follows, using a customary nomenclature:

From the aryl ketones:

acetophenone; propiophenone; butyrophenone; 1-acetonaphthone; 2-acetonaphthone; o-methoxyacetophenone; o-ethoxyacetophenone; o-propoxyacetophenone; o-benzyloxyacetophenone; p-tert-butylacetophenone; 2-acetylpyridine; p-cyanoacetophenone; phenyl benzyl ketone; phenyl o-tolylmethyl ketone; phenyl m-tolylmethyl ketone; phenyl p-tolylmethyl ketone; 2-butanone; 2-pentanone; 2-hexanone; 2-heptanone; 2-octanone; cyclohexyl methyl ketone; cyclohexyl benzyl ketone; 2-chloroacetophenone; 2-bromoacetophenone; 2-bromo-3'-chloroacetophenone; 2-chloro-3'-chloroacetophenone; 2-bromo-3'-bromoacetophenone; 2-bromo-3'-fluoroacetophenone; 2-bromo-3'-methylacetophenone; 2-bromo-3'-ethylacetophenone; 2-bromo-3'-propylacetophenone; 2-bromo-3'-propoxyacetophenone; 2-bromo-3'-butoxyacetophenone; 2-bromo-4'-chloroacetophenone; 2-bromo-4'-bromoacetophenone; 2-bromo-4'-fluoroacetophenone; 2-bromo-4'-methylacetophenone; 2-bromo-4'-ethylacetophenone; 2-bromo-4'-propylacetophenone; 2-bromo-4'-butylacetophenone; 2-bromo-4'-methoxyacetophenone; 2-bromo-4'-ethoxyacetophenone; 2-bromo-4'-propoxyacetophenone; 2-bromo-4'-butoxyacetophenone; 2-bromo-2'-chloroacetophenone; 2-bromo-2'-bromoacetophenone; 2-bromo-2'-fluoroacetophenone; 2-bromo-2'-methylacetophenone; 2-bromo-2'-ethylacetophenone; 2-bromo-2'-propylacetophenone; 2-bromo-2'-butylacetophenone; 2-bromo-2'-methoxyacetophenone; 2-bromo-2'-ethoxyacetophenone; 2-bromo-2'-propoxyacetophenone; 2-bromo-2'-butoxyacetophenone; 2-bromo-2'-fluoro-3'-methoxyacetophenone; 2-bromo-2'-methoxy-2'-methylacetophenone; 2-bromo-2',3'-dimethoxyacetophenone; 2-bromo-2'-ethoxy-3'-methoxyacetophenone; 2-bromo-2',3'-dichloroacetophenone; 2-bromo-2'-bromo-3'-chloroacetophenone; 2-bromo-3'-chloro-2'-fluoroacetophenone; cyclopentenone; 1,3-cyclopentanedione; cyclohexenone; 4-cyclopentene-1,3-dione; 3-oxopyrrolidine; 3-oxopiperidine; 3-oxoquinuclidine; 2-bromo-3'-chloro-2'-fluoroacetophenone; 2-bromo-3'-chloro-2'-methylacetophenone; 2-bromo-3'-chloro-2'-methoxyacetophenone; 2-bromo-3'-chloro-2'-ethoxyacetophenone; 2-bromo-3'-bromo-4'-chloroacetophenone; 2-bromo-2',4'-dibromoacetophenone; 2-bromo-2'-bromo-4'-methylacetophenone; 2-bromo-2'-bromo-4'-methoxyacetophenone; 2-bromo-4'-chloro-2'-fluoroacetophenone; 2-bromo-2',4'-difluoroacetophenone; 2-bromo-4'-chloro-2'-fluoroacetophenone; 2-bromo-2'-fluoro-4'-methylacetophenone; 2-bromo-2'-fluoro-4'-methoxyacetophenone; 2-bromo-4'-ethoxy-2'-fluoroacetophenone; 2-bromo-4'-chloro-2'-ethoxyacetophenone; 2-bromo-4'-bromo-2'-ethoxyacetophenone; 2-bromo-4'-fluoro-2'-ethoxyacetophenone; 2-bromo-4'-methyl-2'-ethoxyacetophenone; 2-bromo-4'-methoxy-2'-ethoxyacetophenone; 2-bromo-2',4'-diethoxyacetophenone; 2-bromo-4'-chloro-3'-ethoxyacetophenone; 2-bromo-3'-ethoxy-4'-methylacetophenone; 2-bromo-3'-ethoxy-4'-methoxyacetophenone; 2-bromo-3',4'-diethoxyacetophenone; 2-bromo-5'-bromo-3'-chloroacetophenone; 2-bromo-3',5'-dibromoacetophenone; 2-bromo-5'-bromo-3'-fluoroacetophenon; 2-bromo-5'-bromo-3'-ethoxyacetophenone; 2-bromo-3'-chloro-5'-ethoxyacetophenone; 2-bromo-3'-bromo-5'-ethoxyacetophenone; 2-bromo-5'-ethoxy-3'-fluoroacetophenone; 2-bromo-5'-ethoxy-3'-methylacetophenone; 2-bromo-5'-ethoxy-3'-methoxyacetophenone; 2-bromo-3',5'-dimethoxyacetophenone; 2-bromo-3',5'-diethoxyacetophenone; 2-bromo-3',5'-dichloroacetophenone; 2-bromo-3',5'-difluoroacetophenone; 2-bromo-2',6'-dichloroacetophenone; 2-bromo-2',4',6'-trichloroacetophenone; 2-bromo-3',4',5'-trichloroacetophenone; 4-bromoacetyl-2-methylthiazole; 4-bromoacetyl-2-trifluoromethylthiazole; 1-bromofluorenone.

From the heteroaryl ketones:

azolyl phenyl ketones; 1,2,3,4-tetrahydronaphthalen-1-one-indanone; 1-cyclohexylethan-1-one; 2-ether-1-arylethanone; 2-(triorganosilyl)oxyalkyl; arylethanone; 2-acylthiophene; 2-acylfuran; 1-(2-thienyl)-3-chloropropanone; 1-(2-furanyl)-3-chloroethanone; 1-(2-furryanal)-3-bromoethanone.

Heteroaryl ketones are particularly preferred and the following compounds are very particularly preferred: 1-(2-thienyl)-3-chloropropanone; 1-(2-furanyl)-3-chloroethanone; 1-(2-furanyl)-3-bromoethanone.

Optionally substituted, saturated or unsaturated alkyl ketones are also perfectly suitable for reduction by the process of the invention.

The invention also makes it possible to reduce optionally substituted, saturated or unsaturated carbocyclic ketones, particularly alpha-tetralones.

The process for the asymmetric reduction of the compounds of formula (VI) takes place under the following operating conditions:

the compounds of formula (VI) are added slowly over a period of between 0.5 and 10 hours, with stirring;

the temperature is between 0° C. and 75° C.; and the amount of prochiral ketone is 10 to 1000 times greater than that of the amino alcohol of formula (IV) used in the reaction.

In one preferred embodiment of the invention, the ketone used is 1-(2-thienyl)-3-chloropropanone and is added in an amount 50 to 100 times greater than that of the optically active compound α,α-diphenylpyrrolidinemethanol, the reaction taking place at a temperature of 40° C. over 1.5 hours.

The optically active alcohol of formula (VII) is isolated by treating the reaction medium according to the methods described in the literature and familiar to those skilled in the art.

The invention further relates to the use of the complex of formula (V), prepared in situ, for the reduction of ether oximes of general formula (VIII) to the corresponding optically active amines of general formula (IX):

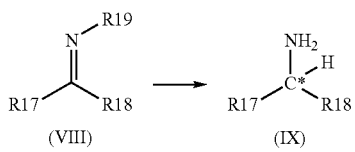

The compounds of formulae (VIII) and (IX) are defined as follows:

$R_{17}$ and $R_{18}$ are different and the chirality of the secondary amine obtained is defined by the carbon atom carrying the amine group.

$R_{17}$ and $R_{18}$ are inert to reduction and are optionally substituted organic radicals which together can form a saturated or unsaturated ring.

$R_{19}$ is an alkoxy, an aryloxy or an arylalkoxy.

The process for the asymmetric reduction of the compounds of formula (VIII) takes place under the same operating conditions as above.

The optically active amine of formula (IX) is isolated by treating the reaction medium according to the methods described in the literature and familiar to those skilled in the art.

Other advantages and characteristics of the invention will become apparent from the Examples below, which are given without implying a limitation.

EXAMPLE 1

Preparation of the HCBS-BH$_3$ Complex in situ: without LiCl Asymmetric Reduction: 20% of (R)-DPP 0.33 g of NaBH$_4$ in 5 ml of THF is placed in a 100 ml four-necked flask under nitrogen.

1.44 ml of diethylaniline (DEA) and 5 ml of THF are added at 20° C., with stirring.

The medium is cooled to 5° C. and 855 µl (1.05 eq.) of dimethyl sulfate (Me$_2$SO$_4$) are added dropwise over 30 min.

The reaction medium is maintained at 20° C. for 1 hour.

0.43 g of (R)-diphenylprolinol is added at 20° C.

The mixture is maintained at 20° C. for 1 hour.

Asymmetric Reduction

The above medium is heated to 40° C.

A solution of 1.5 g of 3-chloro-1-(2-thienyl)propanone in 5 ml of THF is added slowly over 1 h 30 min.

When the introduction has ended, the medium is cooled to 10° C.

It is hydrolyzed with 9 ml of water and stirred for 1 hour at 20° C.

It is decanted.

The organic phase is washed three times with phosphoric acid (1.3 g in 5 ml of water).

The organic phase is washed with 5 ml of water.

The organic phase is washed with 5 ml of saturated NaHCO$_3$ solution.

The organic phase is finally washed with 5 ml of water.

The organic phase is dried over MgSO$_4$ and then concentrated to dryness under vacuum.

An orange oil is obtained.

Yield: quantitative

Enantiomeric excess: 93.8%

Chemical purity: 98%

EXAMPLE 2

Preparation of the HCBS-BH$_3$ Complex in situ: without LiCl Asymmetric Reduction: 5% of (R)-DPP 18.9 g (0.501 mol) of NaBH$_4$ in 200 ml of THF are placed in a 500 ml jacketed reactor under nitrogen.

85 ml (0.521 mol) of diethylaniline (DEA) and 45 ml of THF are added at 20° C., with stirring.

The medium is heated to 40° C.

65.9 g (0.521 mol) of dimethyl sulfate (Me$_2$SO$_4$) are added dropwise.

The reaction medium is maintained at 40° C. for 45 min.

The medium is cooled to 32° C.

5.08 g (0.02 mol) of (R)-diphenylprolinol solubilized in 15 ml of THF are added.

The reaction medium is heated to 40° C. and stirred for 30 min.

The medium is cooled to 32° C.

Asymmetric Reduction 70 g (0.401 mol) of 3-chloro-1-(2-thienyl)propanone are added slowly over 2 h 15 min.

The reaction medium is stirred at 32° C. for 45 min.

The medium is cooled to 15° C. and hydrolyzed with an aqueous solution of 89 g of K$_2$CO$_3$ in 390 ml of water.

The medium is heated to 27° C. and stirred for 1 h 30 min.

It is decanted and the different phases are separated.

The product phase is concentrated to dryness under vacuum.

A colorless clear liquid is obtained.

Yield: 95%

Enantiomeric excess: 94.5%

EXAMPLE 3

Preparation of the HCBS-BH$_3$ Complex in situ: with LiCl Asymmetric Reduction: 5% of (R)-DPP 11.4 g (0.301 mol) of NaBH$_4$ in 150 ml of THF are placed in a 500 ml jacketed reactor under nitrogen.

50.8 ml (0.313 mol) of diethylaniline (DEA) are added at 20° C., with stirring.

The medium is heated to 37° C. and 29.6 ml (0.313 mol) of dimethyl sulfate (DMS) are then added over 45 min.

The reaction medium is stirred at 40° C. for 30 min.

The medium is cooled to 32° C. and 1.33 g (0.0313 mol) of LiCl are added.

The reaction medium is stirred for 30 min.

A solution of 3.5 g (0.012 mol) of (R)-diphenylprolinol in 55 ml of THF is added and the mixture is stirred for 30 min.

Asymmetric Reduction 42 g (0.24 mol) of 3-chloro-1-(2-thienyl)propanone are added slowly to the above medium (temperature: 32° C.) over 1 h.

The reaction medium is stirred for 30 min.

The reaction medium is cooled to room temperature and hydrolyzed with an aqueous solution of 53.2 g of $K_2CO_3$ in 233 ml of water.

The medium is transferred to a 500 ml reactor.

It is decanted and the aqueous phase is discarded.

The product phase is concentrated to dryness under vacuum.

A colorless clear liquid is obtained.

Yield: 94.5%

Enantiomeric excess: 94%

EXAMPLE 4

Preparation of the HCBS-BH$_3$ Complex in situ: without LiCl Asymnmetric Reduction: 1% of (R)-DPP 18.2 g (0.481 mol) of NaBH4 in 308 ml of THF are placed in a 500 ml jacketed reactor under nitrogen.

81.3 ml (0.501 mol) of diethylaniline (DEA) are added at 20° C., with stirring.

The medium is heated to 37° C. and 47.4 ml (0.501 mol) of dimethyl sulfate (DMS) are then added over 45 min.

The reaction medium is stirred at 40° C. for 30 min.

The medium is cooled to 32° C.

The reaction medium is stirred for 30 min.

A solution of 1.02 g (0.004 mol) of (R)-diphenylprolinol in 55 ml of THF is added and the mixture is stirred for 30 min.

Asymmetric Reduction 70 g (0.401 mol) of 3-chloro-1-(2-thienyl)propanone are added slowly over 2 h 00 min.

The reaction medium is stirred at 40° C. for 30 min.

The medium is cooled to 20° C. and hydrolyzed with an aqueous solution of 70 g of $K_2CO_3$ in 350 ml of water at 15° C.

The THF is driven off at 75° C. under atmospheric pressure and then under vacuum.

280 ml of toluene are added and the mixture is cooled to 30° C.

It is decanted and the different phases are separated.

The organic phase is washed with 210 ml of water.

It is decanted and the different phases are separated.

The organic phase is dried over $MgSO_4$ and then concentrated to dryness under vacuum.

A colorless clear liquid is obtained.

Yield: 95%

Enantiomeric excess: 86.1%

EXAMPLE 5

Preparation of the HCBS-BH$_3$ Complex in situ: with LiCl Asymmetric Reduction: 2% of (R)-DPP 18.2 g (0.481 mol) of NaBH$_4$ in 150 ml of THF are placed in a 500 ml jacketed reactor under nitrogen.

81.3 ml (0.501 mol) of diethylaniline (DEA) are added at 20° C., with stirring.

The medium is heated to 37° C. and 47.4 ml (0.501 mol) of dimethyl sulfate (DMS) are then added over 45 min.

The reaction medium is stirred at 40° C. for 30 min.

The medium is cooled to 32° C. and 3.4 g (0.0802 mol) of LiCl are added.

The reaction medium is stirred for 30 min.

A solution of 2.03 g (0.018 mol) of (R)-diphenylprolinol in 55 ml of THF is added and the mixture is stirred for 30 min.

Asymmetric Reduction 70 g (0.4 mol) of 3-chloro-1-(2-thienyl)propanone are added slowly to the above medium (temperature: 32° C.) over 1 h.

The reaction medium is stirred for 30 min.

The reaction medium is cooled to room temperature and hydrolyzed with an aqueous solution of 88.7 g of $K_2CO_3$ in 388 ml of water.

The medium is transferred to a 500 ml reactor.

It is decanted and the aqueous phase is discarded.

The organic phase is concentrated to dryness under vacuum.

A colorless clear liquid is obtained.

Yield: 97%

Enantiomeric excess: 92.3%

EXAMPLE 6

Preparation of the HCBS-BH$_3$ Complex in situ: without LiCl Asymmetric Reduction: 2% of (R)-DPP 1.82 g (0.0481 mol) of NaBH$_4$ in 24 ml of THF are placed in a 100 ml four-necked flask under nitrogen.

8.13 ml (0.0501 mol) of diethylaniline (DEA) are added at 20° C., with stirring.

The medium is heated to 40° C.

6.32 g (0.0501 mol) of dimethyl sulfate (Me$_2$SO$_4$) are added dropwise.

The reaction medium is maintained at 40° C. for 45 min.

The medium is cooled to 32° C.

203.1 mg (0.0008 mol) of (R)-diphenylprolinol solubilized in 4 ml of THF are added.

The reaction medium is heated to 40° C. and stirred for 30 min.

The medium is cooled to 32° C.

Asymmetric Reduction

This reduction step uses the same protocol as that of Example 4 on an amount of 7 g (0.0401 mol) of 3-chloro-1-(2-thienyl)propanone.

A colorless clear liquid is obtained.

Yield: 95%

Enantiomeric excess: 90.6%

EXAMPLE 7

Preparation of the HCBS-BH$_3$ Complex in situ: with LiCl Asymmetric Reduction: 1% of (R)-DPP 1.82 g (0.0481 mol) of NaBH$_4$ in 25 ml of THF are placed in a 100 ml four-necked flask under nitrogen.

8.13 ml (0.0501 mol) of diethylaniline (DEA) are added at 20° C., with stirring.

The medium is heated to 40° C.

6.32 g (0.0501 mol) of dimethyl sulfate (Me$_2$SO$_4$) are added dropwise.

The reaction medium is maintained at 40° C. for 45 min.

339.8 mg (0.008 mol) of LiCl are added to the reaction medium.

203.1 mg (0.0008 mol) of (R)-diphenylprolinol solubilized in 6 ml of THF are added.

The reaction medium is heated to 40° C. and stirred for 30 min.

Asymmetric Reduction

This reduction step uses the same protocol as that of Example 5, carried out at 40° C. on an amount of 7 g (0.0401 mol) of 3-chloro-1-(2-thienyl)propanone.

A colorless clear liquid is obtained.
Yield: 95%
Enantiomeric excess: 90.9%

The results of the different experiments are summarized in Table I below:

TABLE I

| | | Preparation of the HCBS.BH$_3$ complex | | | |
|---|---|---|---|---|---|
| | | Without LiCl | | With LiCl | |
| Ex. | % (R)-DPP | Yield (%)/ Temp. (° C.) | e.e. (%) | Yield (%)/ Temp. (° C.) | e.e. (%) |
| 1 | 20 | 99/40° C. | 93.8 | | |
| 2 | 5 | 95/32° C. | 94.5 | | |
| 3 | 5 | | | 94/42° C. | 94 |
| 6 | 2 | 95/32° C. | 90.6 | | |
| 5 | 2 | | | 97/32° C. | 92.3 |
| 4 | 1 | 95/40° C. | 86.1 | | |
| 7 | 1 | | | 95/40° C. | 90.9 |

The results show that, in the presence of a small amount of (R)-DPP, LiCl makes it possible to maintain a high yield and a high enantiomeric excess.

The invention claimed is:

1. A process for in situ preparation of a chiral compound from an oxazaborolidine-borane complex, comprising the following steps:

1) adding to a suspension of a metal borohydride defined by formula (I):

$$MBH_4 \quad (I)$$

in which:
M a metal ion is selected from the group consisting of sodium, potassium, lithium, and zinc:
a) a Lewis base of general formula (II) below:

$$R_1\text{-}A\text{-}(R_2)_n \quad (II)$$

in which:
$R_1$ and $R_2$, which are identical or different, are selected from the group consisting of an hydrogen atom, an optionally substituted, linear alkyl, an optionally substituted branched alkyl, an optionally substituted aryl, an alkylaryl, a $C_4$-$C_7$ cycloalkyl, and $R_1$ and $R_2$ can together form a $C_1$-$C_7$ alkyl chain or an optionally substituted $C_2$-$C_7$ carbocycle;
n is equal to 1 or 2; and
A is an atom selected from the group consisting of a nitrogen, oxygen, sulfur and phosphorus; and
b) an inorganic acid ester of general formula (III) below:

$$R_3\text{—}X \quad (III)$$

in which:
X is selected from the group consisting of a sulfonyloxy ester group (—OS(O)$_2$OR$_4$), a sulfonate (—OS(O)R$_5$) and a sulfite (—OS(O)OR$_5$); and
$R_3$, $R_4$ and $R_5$, which are identical or different, are selected from the group consisting of a linear or branched alkyl, said alkyl being optionally substituted by a substituent selected from the group consisting of a halogen atom, an aryl, a heterocycle, a heteroaryl, an alkoxy group, an alkylthio group, an alkylaryl group a $C_4$-$C_7$ cycloalkyl, and $R_4$ and $R_5$ together are selected from a $C_1$-$C_7$ alkyl chain and an optionally substituted $C_1$-$C_7$ carbocycle;

2) and then, adding to the product obtained after step 1 an optically active amino alcohol of general formula (IV) below:

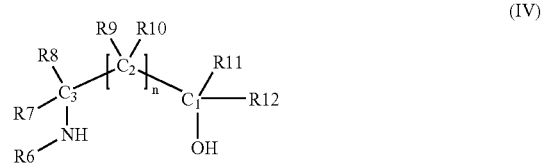

(IV)

in which:
$R_6$ is selected from the group consisting of a hydrogen atom, a linear or branched $C_{1-8}$ lower alkyl group; a $C_{1-15}$ arylalkyl group, and a $C_{1-15}$ arylalkyl group substituted by a substituent selected from the group consisting of C1-C5 alkyl and $C_{1-5}$ alkoxy;
$R_7$, $R_8$, $R_9$, $R_{10}$, $R_{11}$ and $R_{12}$, which are identical or different, independently are selected from the group consisting of a hydrogen atom, a $C_{1-8}$ lower alkyl group, a $C_{6-12}$ aryl group, an aryl group substituted by a $C_{1-5}$ alkyl; a $C_{7-12}$ arylalkyl group, an arylalkyl group substituted by a $C_{1-5}$ alkyl, with the proviso that $R_6$ and $R_7$ are different;
$R_6$ and $R_7$, or $R_7$ and $R_{11}$, or $R_8$ and $R_9$, or $R_{10}$ and $R_{11}$ together can form a $C_{3-6}$ lower alkylene group, a substituted $C_{3-6}$ lower alkylene group, $R_8$ and $R_9$ together can form an alkylene group that is optionally substituted or fused with a benzene ring;
n is equal to 0, 1, 2 or 3; and
at least one of $C_1$, $C_2$ and $C_3$ is an asymmetric carbon atom, thereby obtaining said chiral compound.

2. The process of claim 1, wherein said compound of formula (II) is a linear or cyclic ether; a secondary or tertiary; a linear or cyclic thioether; an amino ether.

3. The process of claim 1, wherein said compound of formula (III) is selected from the group consisting of a dialkyl sulfate, a sulfuric acid bisaryloxyalkyl ester, a bis-alkoxysulfonyloxyalkane, a dioxathiolane dioxide and dimethyl sulfate.

4. The process of claim 1, wherein, the amounts of Lewis base and inorganic ester are ranging between 1 and 2 equivalents, based on the metal borohydride.

5. The process of claim 1, wherein the compounds (I), (II) and (III) are brought into contact in step 1) in any order at a temperature ranging between 0° C. and 75° C. and the resulting reaction medium is stirred at room temperature for a period of time ranging between 0.5 and 4 hours.

6. The process of claim 1, further comprising adding, in step 2) to the product obtained after step 1):
a halide defined by formula (X):

$$M_1\text{-}Y \quad (X)$$

in which:
$M_1$ is selected from a sodium ion, a potassium ion, a lithium ion, an ammonium group and a phosphonium group; and
Y is a halogen atom selected from chlorine, bromine, fluorine and iodine;
and then the optically active amino alcohol of formula (IV).

7. The process of claim 6, wherein $M_1$ is an ammonium group selected from the group consisting of tetraalkylammonium, pyridinium, alkylpiperidinium, alkylpiperazinium, alkylpyrrolidinium and tetraalkylanilinium.

8. The process of claim 6, wherein $M_1$ is a phosphonium group selected from arylphosphonium and alkylarylphosphonium.

9. The process of claim 6, wherein the halide of formula (X) is lithium chloride.

10. The process of claim 1, wherein n is equal to zero in formula (IV) which is of general formula (IVa):

$$\text{(IVa)}$$

in which:
$R_6$, $R_7$, $R_8$, $R_{11}$ and $R_{12}$, are as previously defined; and
At least one of $C_1$ and $C_2$ is an asymmetric carbon atom.

11. The process of claim 10, wherein said optically active product of formula (IVa) is (S)—or (R)-β,β-diphenyl-2-pyrrolidinylmethanol.

12. The process of claim 1, wherein n is equal to 1 in formula (IV) which is of general formula (IVb):

$$\text{(IVb)}$$

in which:
$R_6$, $R_7$, $R_8$, $R_9$, $R_{10}$, $R_{11}$ and $R_{12}$, are as previously defined
At least one of $C_1$, $C_2$ and $C_3$ is an asymmetric carbon atom.

13. The process of claim 12, wherein said optically active product of formula (IVb) is selected from (S)—or (R)-β,β-diphenyl-2-pyrrolidinylethanol; (S)—or (R)-β,β-di(t-butyl)-2-piperidinylethanol; and (S)—or (R)-2-phenyl-4-hydroxypiperidine.

14. The process of claim 1, wherein n is equal to 2 in formula (V) which is of general formula (IVc):

$$\text{(IVc)}$$

in which:
$R_6$, $R_7$, $R_8$, $R_9$, $R_{10}$, $R_{11}$ and $R_{12}$ are as previously defined and $R_{13}$ and $R_{14}$, which are identical or different, independently are selected from a hydrogen atom, a $C_{1-8}$ lower alkyl; a $C_{6-12}$ aryl; a $C_{7-12}$ arylalkyl; a $C_{6-12}$ aryl substituted by a $C_{1-5}$ alkyl; a $C_{7-12}$ arylalkyl substituted by a $C_{1-5}$ alkyl, with the proviso that $R_7$ and $R_8$ are different; and At least one of $C_1$, $C_2$, $C_3$ and $C_4$ is an asymmetric carbon atom.

15. The process of claim 1, wherein the amount of compound of formula (IV) used in the reaction is ranging between 0.005 and 0.2 equivalent, based on the metal borohydride.

16. The process of claim 1, wherein the compound of formula (IV) is optically active α,α-diphenylpyrrolidin-2-yl-methanol.

17. The process of claim 1, used for the synthesis of chiral alcohols, comprising, further to the in situ preparation of the complex according to claim 1, adding a ketone to be reduced.

18. The process of claim 17, wherein said complex is a chiral compound of general formula (V):

$$\text{(V)}$$

in which:
$R_6$, $R_7$, $R_8$, $R_9$, $R_{10}$, $R_{11}$, $R_{12}$ and n are as defined in formula (IV) and at least one of $C_1$, $C_2$ and $C_3$ is an asymmetric carbon atom.

19. The process of claim 17, wherein said ketone is of general formula (VI) below and is reduced to an optically active alcohol of general formula (VII) below:

$$\text{(VI)} \quad \text{(VII)}$$

in which $R_{15}$ and $R_{16}$ are different, are inert to reduction and are optionally substituted organic radicals which together can form a saturated or unsaturated ring.

20. The process of claim 19, wherein the asymmetric reduction of the compound of formula (VI) takes place under the following operating conditions:
adding the compound of formula (VI) slowly over a period of time ranging between 0.5 and 10 hours, under stirring;
maitaining the temperature between 0° C. and 75° C.; and
the amount of ketone is from 10 to 1000 times greater than that of the amino alcohol of formula (IV) used in the reaction.

21. The process of claim 19, wherein the compound of formula (VI) is 1-(2-thienyl)-3-chloropropanone and is added in an amount 50 to 100 times greater than that of the optically active compound α,α-diphenylpyrrolidin-2-yl-methanol.

22. The process of claim 18, comprising using the complex of formula (V), prepared in situ, to reduce the ether oxime of general formula (VIII) below to the corresponding optically active amine of general formula (IX):

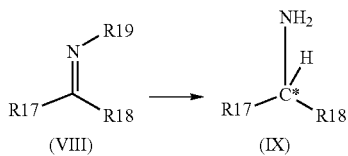

in which:

R$_{17}$ and R$_{18}$ are different and the chirality of the secondary amine obtained is defined by the carbon atom carrying the amine group;

R$_{17}$ and R$_{18}$ are inert to reduction, are organic radicals independently substituted by any group and together can form a saturated or unsaturated ring; and R$_{19}$ is an alkoxy, an aryloxy or an arylalkoxy.

23. The process of claim 1, wherein the C$_{1-8}$ lower alkyl group, is selected from the group consisting of methyl, ethyl, n-propyl, isopropyl, n-butyl, isobutyl, sec-butyl, tert-butyl and pentyl; the C$_{1-15}$ arylalkyl group is selected from the group consisting of benzyl, phenylethyl and methylbenzyl; the C$_{1-15}$ arylalkyl group is substituted by a C$_{1-5}$ alkyl selected from the group consisting of methyl, ethyl, n-propyl, isopropyl, n-butyl, sec-butyl, tert-butyl, and pentyl; the C$_{1-15}$ arylalkyl group is substituted by a C$_{1-5}$ alkoxy selected from the group consisting of methoxy, ethoxy, propoxy, butoxy and pentoxy.

24. The process of claim 1, wherein said alkylene is selected from the group consisting of methylene, dimethylene, trimethylene, tetramethylene, pentamethylene, o-phenylenemethylene and o-phenylenedimethylene.

25. The process of claim 2, wherein the linear or cyclic ether is selected from tetrahydrofuran and tetrahydropyran; the secondary or tertiary amine is selected from N,N-dimethylamine, N,N-diethylamine, aniline, N,N-diethylaniline and N-ethyl-N-isopropylaniline; the linear or cyclic thioether is dimethyl sulfide; the amino ether is selected from morpholine; and a phosphine.

* * * * *